United States Patent [19]

Krabetz et al.

[11] Patent Number: 4,489,170
[45] Date of Patent: Dec. 18, 1984

[54] OXIDATION CATALYST, ESPECIALLY FOR THE PREPARATION OF METHACRYLIC ACID BY GAS PHASE OXIDATION OF METHACROLEIN

[75] Inventors: Richard Krabetz, Kirchheim; Matthias Schwarzmann, Limburgerhof, both of Fed. Rep. of Germany

[73] Assignee: BASF Aktiengesellschaft, Ludwigshafen, Fed. Rep. of Germany

[21] Appl. No.: 470,942

[22] Filed: Mar. 1, 1983

[30] Foreign Application Priority Data

Mar. 10, 1982 [DE] Fed. Rep. of Germany ....... 3208571

[51] Int. Cl.$^3$ .................... B01J 27/14; C07C 51/16
[52] U.S. Cl. .................... 502/211; 562/534; 562/535
[58] Field of Search .................... 252/435, 437

[56] References Cited

U.S. PATENT DOCUMENTS

| | | | |
|---|---|---|---|
| 3,965,163 | 6/1976 | Oda et al. | 252/435 |
| 4,178,464 | 12/1979 | Sakamoto et al. | 252/435 X |
| 4,212,767 | 7/1980 | Daniel . | |
| 4,261,859 | 4/1981 | Khoobior | 252/437 |
| 4,272,408 | 6/1981 | Daniel . | |
| 4,297,247 | 10/1981 | Krabetz et al. . | |
| 4,305,843 | 12/1981 | Krabetz et al. . | |
| 4,334,116 | 6/1982 | Velenyi et al. | 252/435 X |
| 4,335,018 | 6/1982 | Franz et al. | 252/435 |

FOREIGN PATENT DOCUMENTS

| | | | |
|---|---|---|---|
| 2624134 | 12/1977 | Fed. Rep. of Germany | 502/211 |
| 55-133329 | 3/1979 | Japan | 252/437 |
| 1331423 | 9/1973 | United Kingdom | 502/209 |
| 1473035 | 5/1977 | United Kingdom . | |
| 2001256 | 1/1979 | United Kingdom . | |
| 2040717 | 9/1980 | United Kingdom . | |
| 2046252 | 11/1980 | United Kingdom . | |

*Primary Examiner*—Delbert E. Gantz
*Assistant Examiner*—William G. Wright
*Attorney, Agent, or Firm*—Oblon, Fisher, Spivak, McClelland & Maier

[57] ABSTRACT

Oxidation catalysts which in addition to oxygen ions, with or without $NH_4^+$ ions, contain molybdenum, tungsten, phosphorus and antimony as basic components, in the atomic ratio Mo:W:P:Sb=12:0.1–3:0.1–4:0.1–3, and which are prepared in a conventional manner by combining molybdenum, phosphorus, antimony and tungsten compounds in aqueous solutions or suspensions, removing the water and calcining the residues, the combination being carried out at chloride ion concentrations of less than 0.3 mole per mole of molybdenum and in the presence of ions of monocarboxylic acids of 1 or 2 carbon atoms, dicarboxylic acids or hydroxycarboxylic acids, are particularly suitable for the gas phase oxidation of methacrolein to methacrylic acid.

11 Claims, No Drawings

OXIDATION CATALYST, ESPECIALLY FOR THE PREPARATION OF METHACRYLIC ACID BY GAS PHASE OXIDATION OF METHACROLEIN

Numerous oxidation catalysts, and their use for the preparation of methacrylic acid by gas phase oxidation of methacrolein, have been proposed. However, these catalysts only partially, if at all, meet the requirements for an industrial process in respect of high selectivity, coupled with high methacrolein conversions and high space velocities over long operating periods.

British Pat. No. 2,040,717, for example, discloses catalysts which contain Mo, Cu, P, Sb and Cs and/or Ca. However, these catalysts give an unsatisfactory selectivity of 76% for methacrylic acid formation, at methacrolein conversions of only 75%. British Pat. No. 1,473,035 proposes catalysts which additionally to Mo, Cu and P contain one or more alkali metals selected from the group of Li, Na, K, Rb and Cs, and one or more metals selected from the group of Sb, V, W, Fe, Mn and Sn. It is true that these catalysts give, in sustained operation, methacrolein conversions of up to 91.5% and selectivities of 82%, but the low space velocity of 1,000 $h^{-1}$ and relatively high temperature of 325° C. or more are unsatisfactory. Oxidation catalysts of the type disclosed in British Pat. No. 2,046,252, which contain Mo, P and V, with or without As and Cu or other cationic elements, show, it is true, a high catalytic activity, but only if the catalyst particle size is less than 2 mm—which is undesirable in industrial operation—and if used at the relatively high temperature of 330° C. Oxidation catalysts which are prepared in the presence of high chloride ion concentrations of as much as about 5 equivalents per equivalent of molybdenum, for example the catalysts, containing Mo, P and W, of the type disclosed in U.S. Pat. Nos. 4,212,767 and 4,272,408, or the catalysts, containing Mo, P and Sb, with or without W, disclosed in U.S. Pat. No. 3,965,163, show, it is true, relatively good catalytic activity for short operating periods, but it is difficult to produce reproducibly catalysts of this type which have a long life and are adequately selective. Moreover, the catalysts mentioned tend to give increased formation of acetic acid if they are used in particle sizes which are industrially desirable, namely not less than 3 mm.

British Pat. No. 2,001,256 moreover discloses oxidic catalysts which contain Mo, P, As, Cu and Cr and which are prepared in the presence or absence of a dibasic carboxylic acid, hydroxycarboxylic acid, mannitol or pyrogallol as the reducing agent.

However, the properties of these and the other catalysts mentioned above are generally unsatisfactory if methacrolein which has been prepared by condensing propanal with formaldehyde is used as the raw material in the processes mentioned above for the preparation of methacrylic acid. This methacrolein contains, as impurities attributable to the method of preparation, not only unconverted propanal but also organic amines, dimers of methacrolein and methylpentenal, and even small amounts of these impurities in general lead to a more or less pronounced drop in performance of the catalysts of the type mentioned.

It is an object of the present invention to provide oxidation catalysts, especially for the oxidation of methacrolein to methacrylic acid in the gas phase, which, if industrial grades of methacrolein, and catalyst particle sizes conventionally used industrially in fixed bed reactions, are employed, give high yields and a lower formation of by-products even at high space velocities and over long operating periods.

We have found that this object is achieved by providing the oxidation catalysts according to the present invention, and that oxidation catalysts which in addition to oxygen, with or without $NH_4^+$ ions, contain molybdenum, tungsten, phosphorus and antimony as basic components in the atomic ratio Mo:W:P:Sb=12:0.1–3:0.1–4:0.1–3 and which have been prepared in a conventional manner by combining molybdenum, phosphorus, antimony and tungsten compounds in aqueous solution or suspension, removing the water and calcining the residue, are particularly suitable for gas phase reactions if the combination is carried out at a chloride ion concentration of less than 0.3 mole per mole of molybdenum and in the presence of ions of monocarboxylic acids of 1 to 2 carbon atoms, dicarboxylic acids or hydroxycarboxylic acids. The carboxylic acid ions are preferably derived from formic acid, acetic acid, oxalic acid ad those carboxylic acids which both act as reducing agents and form, with antimony compounds, watersoluble salts or complexes which are difficult to hydrolyze, these last-mentioned carboxylic acids being, in particular, tartaric acid and citric acid. Formic acid, or formic acid in combination with the other carboxylic acids mentioned above, is very particularly preferred. Though catalysts which merely contain the stated components themselves exhibit a good catalytic activity, preferred catalysts contain, as additional components, arsenic and/or copper in amounts of >0 to 1 atom per atom of Mo. Particularly preferred oxidation catalysts are those of the general formula

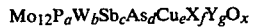

$Mo_{12}P_aW_bSb_cAs_dCu_eX_fY_gO_x$ where
X is one or more elements from the group Nb, Mn, Fe, Sn and Cr,
Y is K, Rb or Cs,
a is 0.1 to 3,
b is 0.1 to 4,
c is 0.1 to 3,
d is >0 to 1,
e is >0 to 1,
f is 0 to 1,
g is 0 to <0.1,
e+f+g is ≦2 and
x is the number of oxygen atoms formally required to saturate the valencies of the other catalyst constituents. The $NH_4^{30}$ ions which may also be present are, for formal reasons, not shown in the formula.

The presence of alkali metals is intrinsically undesirable, since these metals favor the formation of the $MoO_3$ phase at elevated temperatures. Preferably, the amount of K, Rb and Cs in the catalyst should not exceed 0.035 atom per 12 atoms of molybdenum. Of the components X in the above formula, Nb and/or Fe, if appropriate in combination with one of the other elements of group X, is preferred. As regards the exact composition, preferred oxidation catalysts of the above formula are those where
a is 0.5–2,
b is 0.5–3,
c is 0.2–1.5,
d is 0.05–0.5,
e is 0.05–0.8, especially 0.1–0.5,
f is 0–0.8, especially >0–0.5, g is 0–>0.035 and
e+f+g is ≦ 1.

The catalyst components can, if desired, be employed as oxides or acid anhydrides, but in general water-soluble compounds are preferred. Examples of suitable molybdenum compounds and tungsten compounds are ammonium molybdate, phosphomolybdic acids and their salts, ammonium tungstate, phosphotungstic acid and its ammonium salt. Though other salts can also be employed, the above compounds are preferred, in particular ammonium molybdate or phosphomolybdic acid as the molybdenum compound, and phosphotungstic acid as the tungsten compound. In addition to the heteropolyacids mentioned, advantageous sources of phosphorus are phosphoric acid and its ammonium salts. Antimony and the cationic elements can be employed in the form of their chlorides, but the total amount of chloride ions present during preparation of the catalysts should be less than 0.3 mole, especially less than 0.25 mole, per mole of molybdenum, and free hydrochloric acid should not be present. The cationic elements Cu, Mn, Sn, Fe, Nb and Cr can be employed in various forms, for example as oxides, hydroxides or carbonates, for example $Nb_2O_3$, $Sn(II)O$ or $Cu(OH)CO_3$, or as formates, oxalates or acetates. Such salts are preferred to the nitrates. Arsenic is advantageously added as ammonium arsenate or arsenic acid, though other compounds can also be used.

In general, the novel catalysts may be prepared by bringing together the combined solutions of the molybdenum and phosphorus compounds, with oe without an arsenic compound, first with the antimony compound, which is advantageously dissolved or finely dispersed in the aqueous solution of the carboxylic acids, and then with the aqueous solution of the tungsten compound. The additional components which may be employed are in general added after the main components have been combined. The amount of carboxylic acid is in general from 0.02 to 2 moles, preferably from 0.05 to 1.5 moles, per mole of molybdenum. The carboxylic acids can advantageously be added as such, formic acid, acetic acid, tartaric acid and citric acid, and especially formic acid alone or in combination with the other carboxylic acids, being preferred. The carboxylic acid ions assist the formation of a particularly stable form of the phosphorus-containing heteropolyacid and its salts, this form giving, after drying, molding and calcining, a catalytically particularly active structure of the active catalyst.

Drying of the aqueous solution or suspension of the components is in general effected by evaporation in a stirred kettle at below 140° C. or by spray drying at an exit temperature from 80 to 140° C.

After having been dried, the mass obtained is generally milled to a particle size of from 200 to 1,200 μm and molded, if appropriate, after addition of conventional carriers, such as $SiO_2$ or aluminum oxides, with or without lubricants such as graphite, to give balls, tablets, rings or other shapes. These can then be calcined and/or activated in air, under nitrogen or in a slightly reducing atmosphere, at a low gas flow rate and at from 180° to 400° C., preferably from 220° to 380° C., especially from 320° to 360° C. The carriers can also be added during evaporation of the catalyst suspension, as a result of which the catalyst components are deposited on the carriers. Alternatively again, the dried and milled catalyst composition, without addition of carriers, can be calcined at the stated temperatures and then converted to moldings or be applied to carriers, especially to spherical carriers in the form of shells, in a conventional manner, for example by the methods disclosed in U.S. Pat. Nos. 4,305,843 and 4,297,247. After calcining, the catalytically active compositions have solely the structure of a heteropolyacid with defects, or of the salts of such an acid, with characteristic X-ray diffraction lines. The catalysts are particularly suitable for the gas phase oxidation of methacrolein to methacrylic acid under conventoinal conditions, especially if methacrolein prepared by condensing formaldehyde with propanol is used as the starting material.

In the gas phase oxidation of methacrolein, the oxidizing agent used is a gas mixture containing oxygen and steam, which is passed over the catalyst, generally in the form of a fixed catalyst bed. The process is generally carried out under pressures of from 1 to 5 bar, advantageously from 1 to 2.5 bar. In the process, the residence time of methacrolein-containing gas mixtures is, based on standard conditions, from 0.5 to 5 sec.; residence times of from 1 to 3 sec. at from 200° to 340° C., especially from 220° to 320° C., are preferred. In addition to oxygen, methacrolein and water vapor the reaction gases in general contain inert gases, especially nitrogen; the oxygen is in general introduced as air but can also be employed as pure oxygen. Moreover, the reaction gas generally contains carbon oxides, especially if the reaction exit gas remaining after isolation of the methacrylic acid formed is recycled as a diluent, together with unconverted methacrolein, to the oxidation reaction.

In the reaction gas, the molar ratio of methacrolein:oxygen:water:inert gas is generally 1:1–6:1–20:4–50, preferably 1:1.5–4:2–10:6–30. The methacrylic acid can be isolated from the hot reaction exit gases in a conventional manner, generally by chilling with water.

The methacrolein can be obtained by various processes, for example by gas phase oxidation of tert.-butyl-alcohol, isobutylene or $C_4$ mixtures or by condensing propanal with formaldehyde. The use of the novel catalysts is particularly advantageous if the methacrolein employed has been prepared by condensing propionaldehyde with formaldehyde in the presence of salts of secondary amines or with aminals in the presence of acids in aqueous solution. Industrial grades prepared in this way are in general from 94 to 99% pure and in addition to unconverted propionaldehyde contain small amounts of organic amines, such as diethylamine or diethanolamine, methylpentenal and dimers of methacrolein. The purities mentioned are based on anhydrous crude methacrolein, but in practice the material can contain up to 3.5% of water. If unconverted methacrolein and uncondensed reaction exit gases are recycled to the oxidation reaction, the synthesis gas mixture may also contain small amounts of very volatile by-products, such as carbon oxides or acrolein.

In industrial operation, the process is generally carried out in tube bundle reactors in which the catalyst is present in a fixed arrangement. To avoid local overheating, the catalyst activity can be modified so that it increases continuously, or in stages, in the direction of flow in the reaction tube. This can be achieved, for example, by diluting the catalyst with less active or even inactive catalyst or carrier moldings or by employing 2 or more catalysts differing in activity and/or selectivity. It is also possible to carry out the oxidation of methacrolein to methacrylic acid, according to the invention, in a fluidized bed, though fixed catalyst beds are preferred. On working up the reaction gases, which can also be cooled indirectly before scrubbing with water, aqueous solutions of methacrylic acid are obtained, which may additionally contain small amounts of acetic acid, maleic acid and acrylic acid. The methacrylic acid can be extracted from the solutions obtained by means of suitable solvents, for example methyl methacrylate, in a conventional manner, and can either be directly esterified with an alkanol or be distilled out of the extract and separated from the by-products. The unconverted methacrolein can be distilled from the aqueous condensate or, for example, be stripped out with steam, and be recycled to the oxidation reaction.

The novel catalysts also exhibit a good activity and selectivity in other oxidation reactions, for example in the oxidation of acrolein to acrylic acid or in the oxidation of substituted toluene derivatives to substituted benzaldehydes and benzoic acids.

In the Examples which follow, 97-99% pure methacrolein is employed, which in addition to water and propionaldehyde contains small amounts of secondary amines and by-products of the synthesis of methacrolein from propanal and formaldehyde. Parts and percentages are by weight, unless stated otherwise. Parts by volume bear the same relation to parts by weight as that of the liter to the kilogram.

EXAMPLE 1

A solution of 13.2 parts of diammonium phosphate in 100 parts of water is added to an aqueous solution of 212 parts of ammonium heptamolybdate in 600 parts of water. 22.6 parts of antimony trichloride in a mixture of 6 parts of formic acid and 20 parts of water, followed by 15 parts of phosphotungstic acid in 50 parts of water, are added to the solution with vigorous stirring. The mixture is then evaporated to dryness on a water bath under atmospheric pressure, the dry mass is milled to a particle diameter of from 0.4 to 1.2 mm, and the milled material is mixed with 2% of graphite powder and pressed to give 3×3 mm tablets. The tablets are activated by heating them for 6 hours in air at 355° C. The catalyst has the empirical formula $Mo_{12}W_1P_1Sb_1O_{43}$.

80 parts by volume of catalyst tablets are introduced into a reaction tube of 16 mm diameter, which is heated in a salt bath. A gas mixture of 3.3% by volume of methacrolein, 9.1% by volume of oxygen, 29.5% by volume of steam and 58.1% by volume of nitrogen is passed over the catalyst at a space velocity of 1,320 liters (S.T.P.)/liter/hour. After 11 days at a bath temperature of 300° C., the conversion is 92.8 mole %, the selectivity of methacrylic acid formation is 81 mole %, the yield of methacrylic acid is 75 mole % and the yield of acetic acid is 4.1 mole %. Even after 30 days, these values are still achieved.

COMPARATIVE EXAMPLES (A) Example 1 is repeated except that formic acid is replaced by concentrated hydrochloric acid. Under the same test conditions, and after the same running time as in Example 1, the conversion at 300° C. is 82.6 mole %, the selectivity of methacrylic acid formation is 77.4 mole % and the yield of methacrylic acid is 63.9 mole %. Acetic acid is formed in a yield of 6.5 mole %.

(B) In a further experiment, Example 1 is repeated except that no formic acid is added. Under the same test conditions as in Example 1, the conversion is 62 mole %, the selectivity 65 mole % and the yield of methacrylic acid 40.3 mole %.

(C) In a further experiment, Example 1 is repeated, but the amount of formic acid added is increased to 96 parts by volume. Under the same test conditions as in Example 1, the conversion is 10 mole %, the selectivity is 70 mole % and the yield is 7 mole %.

(D) Example 1 is repeated except that no antimony salt is added. Under the same test conditions as in Example 1, at a bath temperature of 300° C., the conversion is found to be 75.5 mole %, the selectivity is 66.9 mole %, the yield of methacrylic acid is 50.5 mole % and the yield of acetic acid is 4.6 mole %.

EXAMPLE 2

An oxidation catalyst is prepared as in Example 1, but in place of formic acid an equal amount of acetic acid (as glacial acetic acid) is employed. Under the same test conditions as in Example 1, at a bath temperture of 300° C., the conversion obtained is 85.8 mole %, the selectivity of methacrylic acid formation is 83.4 mole % and the yield is 71.6 mole %.

EXAMPLE 3

To an aqueous solution of 212 parts of ammonium heptamolybdate in 600 parts of water are added successively a solution of 13.2 parts of diammonium phosphate and 1.3 parts of diarsenic pentoxide hydrate in 100 parts by volume of water, a solution of 22.6 parts of antimony trichloride in a mixture of 6 parts by volume of formic acid and 20 parts by volume of water, a solution of 21 parts of phosphotungstic acid in 50 parts by volume of water and, finally, a solution of 2.5 parts of copper(II) acetate in 100 parts by volume of water. The solution obtained is evaporated, and the dried mass is molded and calcined as described in Example 1. The catalyst has the empirical formula

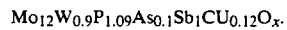
$Mo_{12}W_{0.9}P_{1.09}As_{0.1}Sb_1Cu_{0.12}O_x$.

Under the same test conditions as in Example 1, and at a bath temperature of 318° C., the methacrolein conversion after 7 days is 94.3 mole %, the selectivity is 85.8 mole % and the yield of methacrylic acid is 80.9 mole %. After 30 days, the conversion is 94.1 mole %, the selectivity is 86.2 mole % and the yield is 81.1 mole %. The yield of acetic acid is 2.6%.

EXAMPLES 4 TO 15

Following a procedure similar to Example 3, various oxidation catalysts with various compositions in respect of the components added to the basic components Mo, P, W and Sb are prepared. The compositions are shown in Table 1 below, together with the test results. The added components are employed in the form of the following salts: managanese(II) acetate, iron(II) oxalate, ammonium chromate, niobium(V) oxide, tin(II) oxide.

TABLE 1

| Example | Catalyst | Bath temperature °C. | Conversion mole % | Selectivity mole % | Yield mole % | after . . . days of operation |
|---|---|---|---|---|---|---|
| 4 | $Mo_{12}P_{1.18}W_{1.8}Sb_{1.2}As_{0.1}Cu_{0.25}$ | 319 | 93.8 | 83 | 77.9 | 12 |
| 5 | $Mo_{12}P_{1.1}W_{0.9}Sb_{0.2}As_{0.2}Cu_{0.05}$ | 314 | 92.1 | 85 | 78.3 | 8 |

TABLE 1-continued

| Example | Catalyst | Bath temperature °C. | Conversion mole % | Selectivity mole % | Yield mole % | after ... days of operation |
|---|---|---|---|---|---|---|
| 6 | $Mo_{12}P_{1.1}W_{0.9}Sb_1Cu_{0.25}$ | 284 | 91.7 | 84.6 | 77.5 | 6 |
| 7 | $Mo_{12}P_{1.1}W_{0.9}Sb_1As_{0.2}$ | 302 | 89.6 | 81.3 | 72.8 | 10 |
| 8 | $Mo_{12}P_{1.1}W_{0.9}Sb_1As_{0.2}Cu_{0.1}Mn_{0.1}$ | 318 | 91.7 | 84.5 | 77.4 | 10 |
| 9 | $Mo_{12}P_{1.1}W_{0.9}Sb_1As_{0.2}Cu_{0.1}Nb_{0.4}$ | 324 | 95 | 87.2 | 82.8 | 7 |
| 10 | $Mo_{12}P_{1.1}W_{0.9}Sb_1As_{0.2}Cu_{0.1}Fe_{0.1}$ | 312 | 94.4 | 85.9 | 81.1 | 11 |
| 11 | $Mo_{12}P_{1.1}W_{0.9}Sb_1As_{0.2}Cu_{0.1}Sn_{0.05}$ | 316 | 91.1 | 84.0 | 76.5 | 8 |
| 12 | $Mo_{12}P_{1.1}W_{0.9}Sb_1As_{0.2}Cu_{0.1}$ | 316 | 92.9 | 85.2 | 79.2 | 10 |
| 13 | $Mo_{12}P_{1.2}W_{1.8}Sb_1As_{0.2}Cu_{0.25}K_{0.03}$ | 319 | 95.6 | 81.9 | 78.3 | 7 |
| 14 | $Mo_{12}P_{1.1}W_{0.9}Sb_1As_{0.2}Cu_{0.25}Cs_{0.09}$ | 326 | 92.2 | 81.9 | 75.6 | 4 |
| 15 | $Mo_{12}P_{11}W_{0.9}Sb_1As_{0.2}Cu_{0.25}Rb_{0.03}$ | 319 | 91.5 | 83.5 | 76.4 | 7 |

EXAMPLE 16

A catalyst is prepared by the method of Example 3 except that in place of the antimony trichloride antimony(III) oxide in an amount of 14.6 parts is employed. Under the test conditions of Example 3, but at a bath temperature of 284° C., the conversion is 84.8 mole %, the selectivity is 83.7 mole %, the yield of methacrylic acid is 71 mole % and the yield of acetic acid 0.86 mole %.

EXAMPLES 17 TO 19

Further catalysts were prepared by the method of Example 3, but using tartaric acid, citric cid and oxalic acid in place of formic acid, and were tested. The amounts added, and the test results, are shown in Table 2.

TABLE 2

| Example | Additive | Moles per mole of Mo | Bath temperature °C. | Conversion mole % | Selectivity mole % | Yield mole % |
|---|---|---|---|---|---|---|
| 17 | Tartaric acid | 0.4 | 312 | 87.4 | 84.5 | 73.8 |
| 18 | Citric acid | 0.08 | 300 | 83.5 | 85.2 | 71.2 |
| 19 | Oxalic acid | 0.18 | 316 | 81 | 93.2 | 75.5 |

We claim:

1. An oxidation catalyst of the formula: $Mo_{12}W_{0.1-3}P_{0.1-4}Sb_{0.1-3}O_x$ wherein $x$ is the number of oxygen atoms formally required to saturate the valences of the remaining constituents of the catalyst, prepared by a process comprising:

(a) combining molybdenum, phosphorous, antimony and tungsten compounds in the presence of ions of monocarboxylic acids of one or two carbon atoms, dicarboxylic acids or hydroxycarboxylic acids in an aqueous solution or suspension under conditions such that the amount of said organic acid ranges from 0.02 to 2 moles per mole of molybdenum and the chloride ion concentration in said solution or suspension is less than 0.3 mole per mole of molybdenum;

(b) removing water from the solution or suspension; and (c) calcining the residue obtained.

2. The oxidation catalyst as claimed in claim 1, wherein the carboxylic acid ions are derived from formic, acetic, oxalic, tartaric acid/or citric acid.

3. The oxidation catalyst as claimed in claim 1, wherein arsenic and/or copper, in amounts of from 0 to 1 atom per 12 atoms of molybdenum, are present as additional components of said catalyst.

4. The oxidation catalyst of claim 1, wherein the chloride ion concentration in solution is less than 0.25 mole per mole of molybdenum.

5. The oxidation catalyst of claim 1, wherein the amount of said carboxylic acid in solution ranges from 0.02 to 2 moles per mole of molybdenum.

6. The oxidation catalyst of claim 1, wherein said carboxylic acid is formic acid, acetic acid, oxalic acid, tartaric acid or citric acid.

7. The oxidation catalyst of claim 1 wherein the constituents further comprise ammonium ions.

8. An oxidation catalyst of the formula: $Mo_{12}P_aW_bSb_cAs_dCu_eX_fY_gO_x$ wherein x is at least one element selected from the group consisting of Nb, Mn, Fe, Sn and Cr, and wherein Y is K, Rb or Cs, a is 0.1 to 3, b is 0.1 to 4, c is 0.1 to 3, d is >0 to 1, e is >0 to 1, f is 0 to 1, g is 0 to >0.1, e+f+g is ≦2 and x is the number of oxygen atoms formally required to saturate the valencies of the other catalyst constituents, said catalyst being prepared by (a) combining molybdenum, phosphorous, antimony and tungsten compounds in the presence of ions of monocarboxylic acids of one or two carbon atoms, dicarboxylic acids or hydroxycarboxylic acids in an aqueous solution or suspension under conditions such that the amount of said organic acid ranges from 0.02 to 2 moles per mole of molybdenum and the chloride ion concentration in said solution or suspension is less than 0.3 mole per mole of molybdenum;

(b) removing water from the solution or suspension; and (c) calcining the residue obtained.

9. The oxidation catalyst as claimed in claim 8, wherein the lettered subscripts of the elements of said oxidation catalyst have the following values: a is 0.5–2, b is 0.5–3, c is 0.2–1.5, d is 0.05–0.5, e is 0.05–0.8, f is 0–0.8, g is 0–<0.035, e+f+g is ≦1 and x is as defined in claim 8.

10. A process for the preparation of an oxidation catalyst as claimed in claim 7, comprising:

(a) combining aqueous solutions or suspensions of molybdenum, phosphorus, antimony and tungsten compounds, the combined aqueous material having a chloride ion concentration of less than 0.3 mole per mole of molybdenum and containing from 0.2 to 2 moles of formic acid, acetic acid, oxalic acid, tartaric acid and/or citric acid per mole of molybdenum; (b) removing the water from the resulting mixture; and (c) calcining the residue at a temperature from 180° to 400° C.

11. The process of claim 10 wherein said oxidation catalyst is supported on a carrier.

* * * * *